(12) United States Patent
Fischvogt (10) Patent No.: US 9,351,733 B2
(45) Date of Patent: May 31, 2016

(54) SURGICAL FASTENER APPLIER (71) Applicant: Covidien LP, Mansfield, MA (US)

(72) Inventor: Gregory Fischvogt, Hamden, CT (US)

(73) Assignee: Covidien LP, Mansfield, MA (US)

(*) Notice: Subject to any disclaimer, the term of this patent is extended or adjusted under 35 U.S.C. 154(b) by 182 days.

(21) Appl. No.: 14/134,143

(22) Filed: Dec. 19, 2013

(65) Prior Publication Data

US 2014/0207152 A1    Jul. 24, 2014

Related U.S. Application Data (60) Provisional application No. 61/754,130, filed on Jan. 18, 2013.

(51) Int. Cl.
*A61B 17/10* (2006.01)
*A61B 17/068* (2006.01)
*A61B 17/00* (2006.01)
*A61B 17/064* (2006.01)

(52) U.S. Cl.
CPC ............... *A61B 17/10* (2013.01); *A61B 17/068* (2013.01); *A61B 2017/00367* (2013.01); *A61B 2017/0649* (2013.01)

(58) Field of Classification Search
None
See application file for complete search history.

(56) References Cited

U.S. PATENT DOCUMENTS

| | | | |
|---|---|---|---|
| 3,866,510 A | 2/1975 | Eibes | |
| 4,884,572 A | 12/1989 | Bays | |
| 5,085,661 A | 2/1992 | Moss | |
| 5,171,247 A | 12/1992 | Hughett | |
| 5,171,249 A | 12/1992 | Stefanchik | |
| 5,176,306 A | 1/1993 | Heimerl | |
| 5,207,697 A | 5/1993 | Carusillo | |
| 5,228,256 A | 7/1993 | Dreveny | |
| 5,246,441 A | 9/1993 | Ross | |
| 5,246,450 A | 9/1993 | Thornton | |
| 5,330,487 A | 7/1994 | Thornton | |
| 5,344,061 A | 9/1994 | Crainich | |
| 5,356,064 A | 10/1994 | Green | |
| 5,382,254 A | 1/1995 | McGarry | |
| 5,398,861 A | 3/1995 | Green | |
| 5,403,327 A | 4/1995 | Thornton | |
| 5,433,721 A | 7/1995 | Hooven | |

(Continued)

FOREIGN PATENT DOCUMENTS

| | | |
|---|---|---|
| EP | 0 374 088 | 6/1990 |
| EP | 0 834 280 | 4/1998 |

(Continued)

OTHER PUBLICATIONS

Extended European Search Report corresponding to EP No. 10 01 2659.8, completed Dec. 21, 2010 and mailed Jan. 3, 2011; 3 pages.
Extended European Search Report corresponding to EP No. 10 01 2646.5, completed Feb. 11, 2011 and mailed Feb. 22, 2011; 3 pages.
Extended European Search Report corresponding to EP No. 11 25 0549.0, completed Sep. 9, 2013 and mailed Sep. 17, 2014; 9 pages.

*Primary Examiner* — Tuan V Nguyen (57) ABSTRACT

A surgical fastener applier includes a variable drive mechanism disposed within a housing and operably coupled between an input member and an output member, the variable drive mechanism being transitionable between at least a first condition, wherein rotation of the input member by a fixed amount effects rotation of the output member a first amount, and a second condition, wherein rotation of the input member by the fixed amount effects rotation of the output member a second amount different from the first amount.

14 Claims, 6 Drawing Sheets

(56) References Cited

U.S. PATENT DOCUMENTS

| | | |
|---|---|---|
| 5,439,468 A | 8/1995 | Schulze |
| 5,466,243 A | 11/1995 | Schmieding |
| 5,467,911 A | 11/1995 | Tsuruta |
| 5,474,566 A | 12/1995 | Alesi |
| 5,474,567 A | 12/1995 | Stefanchik |
| 5,522,844 A | 6/1996 | Johnson |
| 5,527,319 A | 6/1996 | Green |
| 5,553,765 A | 9/1996 | Knodel |
| 5,562,685 A | 10/1996 | Mollenauer |
| 5,564,615 A | 10/1996 | Bishop |
| 5,582,615 A | 12/1996 | Foshee |
| 5,582,616 A | 12/1996 | Bolduc |
| 5,584,425 A | 12/1996 | Savage |
| 5,588,581 A | 12/1996 | Conlon |
| 5,601,571 A | 2/1997 | Moss |
| 5,601,573 A | 2/1997 | Fogelberg |
| 5,626,613 A | 5/1997 | Schmieding |
| 5,628,752 A | 5/1997 | Asnis |
| 5,649,931 A | 7/1997 | Bryant |
| 5,662,662 A | 9/1997 | Bishop |
| 5,681,330 A | 10/1997 | Hughett |
| 5,683,401 A | 11/1997 | Schmieding |
| 5,685,474 A | 11/1997 | Seeber |
| 5,697,935 A | 12/1997 | Moran |
| 5,709,692 A | 1/1998 | Mollenauer |
| 5,728,116 A | 3/1998 | Rosenman |
| 5,730,744 A | 3/1998 | Justin |
| 5,732,806 A | 3/1998 | Foshee |
| 5,735,854 A | 4/1998 | Caron |
| 5,741,268 A | 4/1998 | Schutz |
| 5,762,255 A | 6/1998 | Chrisman |
| 5,782,844 A | 7/1998 | Yoon |
| 5,810,882 A | 9/1998 | Bolduc |
| 5,824,008 A | 10/1998 | Bolduc |
| 5,830,221 A | 11/1998 | Stein |
| 5,843,087 A | 12/1998 | Jensen |
| 5,897,564 A | 4/1999 | Schulze |
| 5,904,693 A | 5/1999 | Dicesare |
| 5,910,105 A | 6/1999 | Swain |
| 5,911,722 A | 6/1999 | Adler |
| 5,928,244 A | 7/1999 | Tovey |
| 5,928,252 A | 7/1999 | Steadman |
| 5,931,844 A | 8/1999 | Thompson |
| 5,941,439 A | 8/1999 | Kammerer |
| 5,954,259 A | 9/1999 | Viola |
| 5,961,524 A | 10/1999 | Crombie |
| 5,964,772 A | 10/1999 | Bolduc |
| 5,976,160 A | 11/1999 | Crainich |
| 5,997,552 A | 12/1999 | Person |
| 6,010,513 A | 1/2000 | Tormala |
| 6,013,991 A | 1/2000 | Philipp |
| 6,039,753 A | 3/2000 | Meislin |
| 6,074,395 A | 6/2000 | Trot |
| 6,099,537 A | 8/2000 | Sugai |
| 6,126,670 A | 10/2000 | Walker |
| 6,132,435 A | 10/2000 | Young |
| 6,146,387 A | 11/2000 | Trot |
| 6,183,479 B1 | 2/2001 | Tormala |
| 6,228,098 B1 | 5/2001 | Kayan |
| 6,235,058 B1 | 5/2001 | Huene |
| 6,241,736 B1 | 6/2001 | Sater |
| 6,261,302 B1 | 7/2001 | Voegele |
| 6,296,656 B1 | 10/2001 | Bolduc |
| 6,330,964 B1 | 12/2001 | Kayan |
| 6,387,113 B1 | 5/2002 | Hawkins |
| 6,402,757 B1 | 6/2002 | Moore, III |
| 6,425,900 B1 | 7/2002 | Knodel |
| 6,439,446 B1 | 8/2002 | Perry |
| 6,440,136 B1 | 8/2002 | Gambale |
| 6,450,391 B1 | 9/2002 | Kayan |
| 6,457,625 B1 | 10/2002 | Tormala |
| 6,551,333 B2 | 4/2003 | Kuhns |
| 6,562,051 B1 | 5/2003 | Bolduc |
| 6,572,626 B1 | 6/2003 | Knodel |
| 6,589,249 B2 | 7/2003 | Sater |
| 6,626,916 B1 | 9/2003 | Yeung |
| 6,632,228 B2 | 10/2003 | Fortier |
| 6,652,538 B2 | 11/2003 | Kayan |
| 6,663,656 B2 | 12/2003 | Schmieding |
| 6,695,867 B2 | 2/2004 | Ginn |
| 6,733,506 B1 | 5/2004 | McDevitt |
| 6,743,240 B2 | 6/2004 | Smith |
| 6,749,621 B2 | 6/2004 | Pantages |
| 6,755,836 B1 | 6/2004 | Lewis |
| 6,773,438 B1 | 8/2004 | Knodel |
| 6,824,548 B2 | 11/2004 | Smith |
| 6,837,893 B2 | 1/2005 | Miller |
| 6,840,943 B2 | 1/2005 | Kennefick |
| 6,843,794 B2 | 1/2005 | Sixto |
| 6,869,435 B2 * | 3/2005 | Blake, III ............ A61B 17/1285 606/143 |
| 6,884,248 B2 | 4/2005 | Bolduc |
| 6,887,244 B1 | 5/2005 | Walker |
| 6,893,446 B2 | 5/2005 | Sater |
| 6,905,057 B2 | 6/2005 | Swayze |
| 6,942,674 B2 | 9/2005 | Belef |
| 6,945,979 B2 | 9/2005 | Kortenbach |
| 6,960,217 B2 | 11/2005 | Bolduc |
| 6,966,919 B2 | 11/2005 | Sixto, Jr. |
| 6,988,650 B2 | 1/2006 | Schwemberger |
| 7,000,819 B2 | 2/2006 | Swayze |
| 7,204,847 B1 | 4/2007 | Gambale |
| 7,229,452 B2 | 6/2007 | Kayan |
| 7,261,716 B2 | 8/2007 | Strobel |
| 7,670,362 B2 | 3/2010 | Zergiebel |
| 7,758,612 B2 | 7/2010 | Ship |
| 7,841,502 B2 | 11/2010 | Walberg |
| 7,862,573 B2 | 1/2011 | Darois |
| 7,867,252 B2 | 1/2011 | Criscuolo |
| 7,905,889 B2 | 3/2011 | Catanese |
| 7,931,660 B2 | 4/2011 | Aranyi |
| 8,034,076 B2 | 10/2011 | Criscuolo |
| 8,056,565 B2 | 11/2011 | Zergiebel |
| 8,087,142 B2 | 1/2012 | Levin |
| 8,114,099 B2 | 2/2012 | Ship |
| 8,114,101 B2 | 2/2012 | Criscuolo |
| 8,216,272 B2 | 7/2012 | Ship |
| 8,282,670 B2 | 10/2012 | Shipp |
| 8,328,823 B2 | 12/2012 | Aranyi |
| 8,343,176 B2 | 1/2013 | Criscuolo |
| 8,382,778 B2 | 2/2013 | Criscuolo |
| 8,474,679 B2 | 7/2013 | Felix |
| 8,579,919 B2 | 11/2013 | Bolduc |
| 8,579,920 B2 | 11/2013 | Nering |
| 8,821,514 B2 * | 9/2014 | Aranyi ................ A61B 17/064 606/139 |
| 2003/0009441 A1 | 1/2003 | Holsten |
| 2004/0092937 A1 | 5/2004 | Criscuolo |
| 2004/0133214 A1 * | 7/2004 | Kayan ................ A61B 17/0644 606/142 |
| 2004/0204723 A1 | 10/2004 | Kayan |
| 2006/0129152 A1 | 6/2006 | Ship |
| 2007/0038220 A1 | 2/2007 | Ship |
| 2007/0049947 A1 | 3/2007 | Menn |
| 2007/0049950 A1 | 3/2007 | Theroux |
| 2007/0162030 A1 | 7/2007 | Aranyi |
| 2008/0097523 A1 | 4/2008 | Bolduc |
| 2009/0118776 A1 | 5/2009 | Kelsch |
| 2010/0270354 A1 | 10/2010 | Rimer |
| 2010/0292710 A1 | 11/2010 | Daniel |
| 2010/0292713 A1 | 11/2010 | Cohn |
| 2010/0292715 A1 | 11/2010 | Nering |
| 2011/0071578 A1 | 3/2011 | Colesanti |
| 2011/0079627 A1 | 4/2011 | Cardinale |
| 2011/0087240 A1 | 4/2011 | Shipp |
| 2013/0320059 A1 * | 12/2013 | Gregory ................ B25C 1/008 227/8 |

FOREIGN PATENT DOCUMENTS

| | | |
|---|---|---|
| EP | 1 273 272 | 1/2003 |
| JP | 9149906 | 6/1997 |

* cited by examiner

SURGICAL FASTENER APPLIER

CROSS-REFERENCE TO RELATED APPLICATIONS

This application claims the benefit of and priority to U.S. Provisional Patent Application No. 61/754,130, filed Jan. 18, 2013, the entire disclosure of which is incorporated by reference herein.

BACKGROUND

1. Technical Field

The present disclosure relates to surgical instruments and, more particularly, to a surgical fastener applier configured to deliver and engage various differently-sized surgical fasteners within tissue.

2. Description of Related Art

Many surgical procedures require instruments capable of applying surgical fasteners to tissue to form tissue connections or to secure objects to tissue. For example, during hernia repair it is often desirable to fasten a mesh to body tissue using a surgical fastener. One type of surgical fastener suited for use in affixing mesh to tissue as well as many other surgical procedures, is a coil fastener. Coil fasteners typically have a helically coiled body portion terminating in a tissue-penetrating tip. Examples of coil fasteners and surgical fastener appliers for use therewith are described in U.S. Pat. Nos. 5,830,221 and 5,582,616, both of which are incorporated by reference herein in their entirety.

As can be appreciated, the particular size of the surgical fastener to be used may depend on the procedure to be performed, anatomical considerations, and/or other factors. It would therefore be desirable to provide a surgical fastener applier capable of applying various differently-sized surgical fasteners.

SUMMARY

The present disclosure relates to a surgical fastener applier configured to deliver and engage various differently-sized surgical fasteners within tissue.

According to an aspect of the present disclosure, a surgical fastener applier is provided and includes a housing having an elongated tubular member extending distally from the housing; a trigger coupled to an input member and extending from the housing, the trigger pivotable relative to the housing from a first position to a second position to rotate the input member a fixed amount; a drive shaft extending from the housing and rotatably disposed within the elongated tubular member, the drive shaft retaining at least one surgical fastener thereon, the drive shaft coupled to an output member at a proximal end of the drive shaft such that rotation of the output member effects corresponding rotation of the drive shaft to apply a distal-most surgical fastener to tissue; and a variable drive mechanism disposed within the housing and operably coupled between the input member and the output member, the variable drive mechanism transitionable between at least a first condition, wherein rotation of the input member by the fixed amount effects rotation of the output member a first amount, and a second condition, wherein rotation of the input member by the fixed amount effects rotation of the output member a second amount different from the first amount.

The trigger may include a flange portion defining a plurality of gear teeth and wherein the input member defines a plurality of complementary gear teeth disposed in meshed engagement with the gear teeth of the flange portion of the trigger such that pivoting of the trigger from the first position to the second position rotates the input member the fixed amount.

The drive shaft may include a gear cap disposed at the proximal end of the shaft. The gear cap may define a plurality of gear teeth. The output member may define a plurality of complementary gear teeth disposed in meshed engagement with the gear teeth of the gear cap such that rotation of output member corresponds to rotation of the drive shaft to apply the distal-most surgical fastener to tissue.

The surgical fastener applier may further include a control knob coupled to the variable drive mechanism and may extend from the housing. The control knob may be selectively manipulatable to transition the variable drive mechanism between the first and second conditions.

At least one of the control knob and the housing may include indicia configured to indicate the condition of the variable drive mechanism.

Rotation of the output member by the first amount may effect rotation of the drive shaft sufficiently for applying a relatively small-sized surgical fastener. Rotation of the output member by the second amount may effect rotation of the drive shaft sufficiently for applying a relatively large-sized surgical fastener.

The variable drive mechanism may be transitionable to a third condition, wherein rotation of the input member by the fixed amount effects rotation of the output member a third amount different from the first and second amounts, and wherein rotation of the output member by the third amount effects rotation of the drive shaft sufficiently for applying a relatively medium-sized surgical fastener.

The drive shaft and the at least one surgical fastener may comprise a replaceable cartridge. The replaceable cartridge may be releasably engagable with the surgical fastener applier. The replaceable cartridge may include one of: a first drive shaft retaining a plurality of small-sized surgical fasteners thereon, and a second drive shaft retaining a plurality of relatively large-sized surgical fasteners thereon.

The variable drive mechanism may include first and second cone members and a disc member, each cone member defining an apex portion and a base portion having a diameter greater than that of the apex portion, the disc member interdisposed between the cone members and contacting each of the cone members such that the disc member imparts rotation of the first cone member to the second cone member, the disc member tiltable relative to the cone members to vary relative contact points between the disc member and the first and second cone members to thereby vary a ratio of rotation of the first cone member as compared to rotation of the second cone member.

The input member may be engaged to the first cone member and wherein the output member may be engaged to the second cone member such that tilting the disc member varies a ratio of rotation of the input member as compared to rotation of the output member.

The variable drive mechanism may be continuously transitionable between at least the first and second conditions.

The variable drive mechanism may include first and second pairs of cone members and a belt member disposed about the first and second pairs of cone members. The cone members of the first pair may be disposed about a first shaft and movable relative to one another along the first shaft to vary a first diameter about which the belt is disposed at a first end of the belt, the cone members of the second pair disposed about a second shaft and movable relative to one another along the second shaft to vary a second diameter about which the belt is disposed at a second end of the belt, wherein varying the first and second diameters relative to one another varies a ratio of rotation of the first pair of cone member as compared to rotation of the second pair of cone members.

The input member may be engaged to the first shaft and wherein the output member may be engaged to the second shaft such that varying the first and second diameters relative to one another varies a ratio of rotation of the input member as compared to rotation of the output member.

According to another aspect of the present disclosure, a method of surgery is provided and includes the step of providing a surgical fastener applier including a trigger and a drive assembly, the trigger movable a pre-determined stroke length, the drive assembly including an input member coupled to the trigger, an output member, and a variable drive mechanism operably coupled between the input member and the output member.

The method further includes the steps of coupling a first surgical fastener to the output member, wherein a first amount of rotation of the output member is required to apply the first surgical fastener to tissue; setting an input to output ratio of the variable drive mechanism in accordance with the first amount of rotation of the output member; and moving the trigger the pre-determined stroke length to rotate the output member by the first amount of rotation of the output member to apply the first surgical fastener to tissue.

The method may further include the step of selecting a surgical fastener from the group consisting of: the first surgical fastener, a second surgical fastener requiring a second amount of rotation of the output member to apply the second surgical fastener to tissue, and a third surgical fastener requiring a third amount of rotation of the output member to apply the second surgical fastener to tissue, before coupling the first surgical fastener to the output member.

The first, second, and third surgical fasteners may be different sizes.

The method may further comprise the steps of coupling a second surgical fastener to the output member of the surgical fastener applier, wherein a second amount of rotation of the output member, different from the first amount, is required to apply the second surgical fastener to tissue; setting an input to output ratio of the variable drive mechanism in accordance with the second amount of rotation of the output member; and moving the trigger the pre-determined stroke length to rotate the output member the second amount of rotation of the output member to apply the second surgical fastener to tissue.

The surgical fastener applier may further include a control knob coupled to the variable drive mechanism, and wherein setting the input to output ratio is effected by rotating the control knob.

According to yet another aspect of the present disclosure, a surgical kit is provided and includes first, second, and third cartridges, each cartridge including a drive member having a plurality of surgical fasteners disposed thereon, the first cartridge including relatively small-sized surgical fasteners requiring a first amount of rotation for applying the relatively small-sized surgical fasteners, the second cartridge including medium-sized surgical fasteners requiring a second amount of rotation for applying the medium-sized surgical fasteners, and the third cartridge including relatively large-sized surgical fasteners requiring a third amount of rotation for applying the relatively large-sized surgical fasteners; and a surgical fastener applier.

The surgical fastener applier includes a housing having an elongated tubular member extending distally from the housing; a trigger coupled to an input member and extending from the housing, the trigger pivotable relative to the housing from a first position to a second position to rotate the input member a fixed amount; an output member configured to relesably engage each of the first, second, and third cartridges; and a variable drive mechanism disposed within the housing and operably coupled between the input member and the output member.

The variable drive mechanism is transitionable between a first condition, wherein rotation of the input member by the fixed amount effects rotation of the output member the first amount for applying the relatively small-sized surgical fasteners when the first cartridge is engaged to the output member; a second condition, wherein rotation of the input member by the fixed amount effects rotation of the output member the second amount for applying the medium-sized surgical fasteners when the second cartridge is engaged to the output member; and a third condition, wherein rotation of the input member by the fixed amount effects rotation of the output member the third amount for applying the relatively large-sized surgical fasteners when the third cartridge is engaged to the output member.

BRIEF DESCRIPTION OF THE DRAWINGS

Various embodiments of the presently disclosed surgical fastener applier are described herein with reference to the drawings wherein.

DETAILED DESCRIPTION

Embodiments of a surgical fastener applier in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring to FIGS. 1-3B, an exemplary surgical fastener applier provided in accordance with the present disclosure is shown generally identified by reference numeral 10. Surgical fastener applier 10 is configured to apply various differently-sized helical-shaped coil fasteners to tissue, e.g., relatively small, medium, and large surgical fasteners, depending on a particular purpose. Although the exemplary embodiment is described with respect to a surgical fastener applier for applying coil-shaped fasteners, the features and aspects of the present disclosure are equally applicable for use with any suitable configuration of surgical fastener and/or fastener applier. As can be appreciated, providing a surgical fastener applier 10 capable of applying various differently-sized surgical fasteners obviates the need for multiple surgical fastener appliers corresponding to different sized surgical fasteners.

Figure 1:
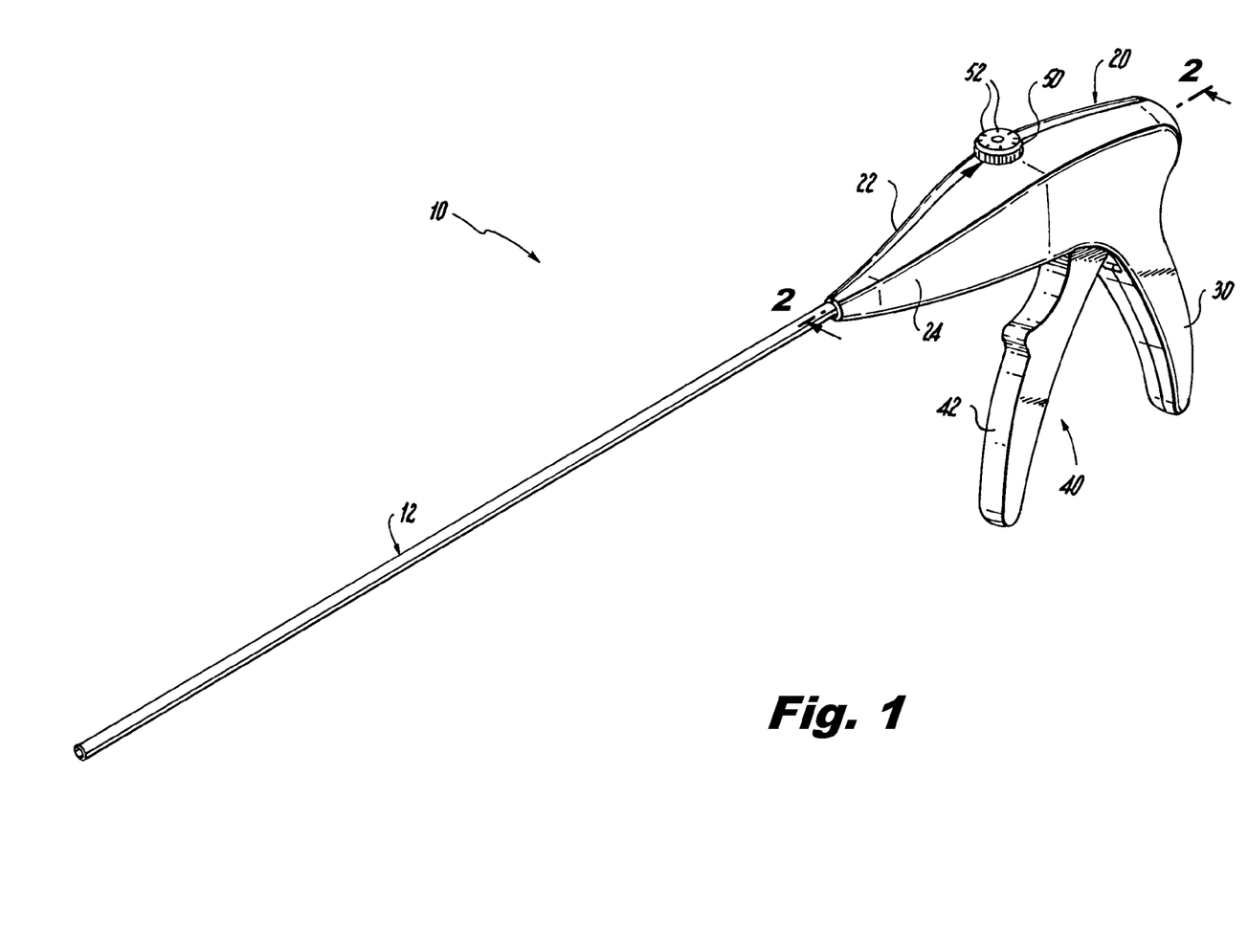
FIG. 1 is a front, perspective view of a surgical fastener applier provided in accordance with the present disclosure.

Surgical fastener applier 10 generally includes a housing 20 having an elongated tubular member 12 extending distally from housing 20. Elongated tubular member 12 is configured for insertion through an access portal (not shown) and/or cannula structure (not shown) for use of surgical fastener applier 10 during minimally-invasive surgical procedures. However, surgical fastener applier 10 may also be configured for use in connection with open surgical procedures.

Continuing with reference to FIGS. 1-3B, housing 20 of surgical fastener applier 10 defines a body portion 22 and a fixed handle 30 extending downwardly from body portion 22 to facilitate gripping housing 20 of surgical fastener applier 10 with a single hand. Body portion 22 of housing 20 houses the inner working components of surgical fastener applier 10, e.g., drive assembly 100. A trigger 40 is pivotably coupled to housing 20 and includes a grasping portion 42 extending from housing 20 adjacent fixed handle 30. Trigger 40 is operably coupled to drive assembly 100 within housing 20 such that, as will be described in greater detail below, movement of trigger 40 relative to fixed handle 30 from a spaced-apart or un-actuated position to a compressed or actuated position drives drive assembly 100 to deploy a surgical fastener 210, 220, 230 from the distal end of elongated tubular member 12. A biasing member, e.g., spring 44, disposed within housing 20 and coupled to trigger 40 serves to bias trigger 40 towards the spaced-apart position.

Housing 20 further includes a control knob 50 mounted on body portion 22 of housing 20. Control knob 50, as will be described in greater detail below, is coupled to drive assembly 100, thus allowing a user to select a desired configuration of drive assembly 100 of surgical fastener applier 10, depending on the particular size surgical fastener(s) 210, 220, 230 (FIGS. 4A-4C) to be applied. For example, control knob 50 may be rotated between a first position corresponding to relatively small-sized surgical fasteners 210 (FIG. 4A), a second position corresponding to medium-sized surgical fasteners 220 FIG. 4B), and a third position corresponding to relatively large-sized surgical fasteners 230 (FIG. 4C). Indicia 52, 24 on control knob 50 and/or housing 20, respectively, may also be provided to permit a user to readily ascertain and confirm the set configuration of drive assembly 100. The operation of control knob 50 will be described in greater detail below.

Figure 2:
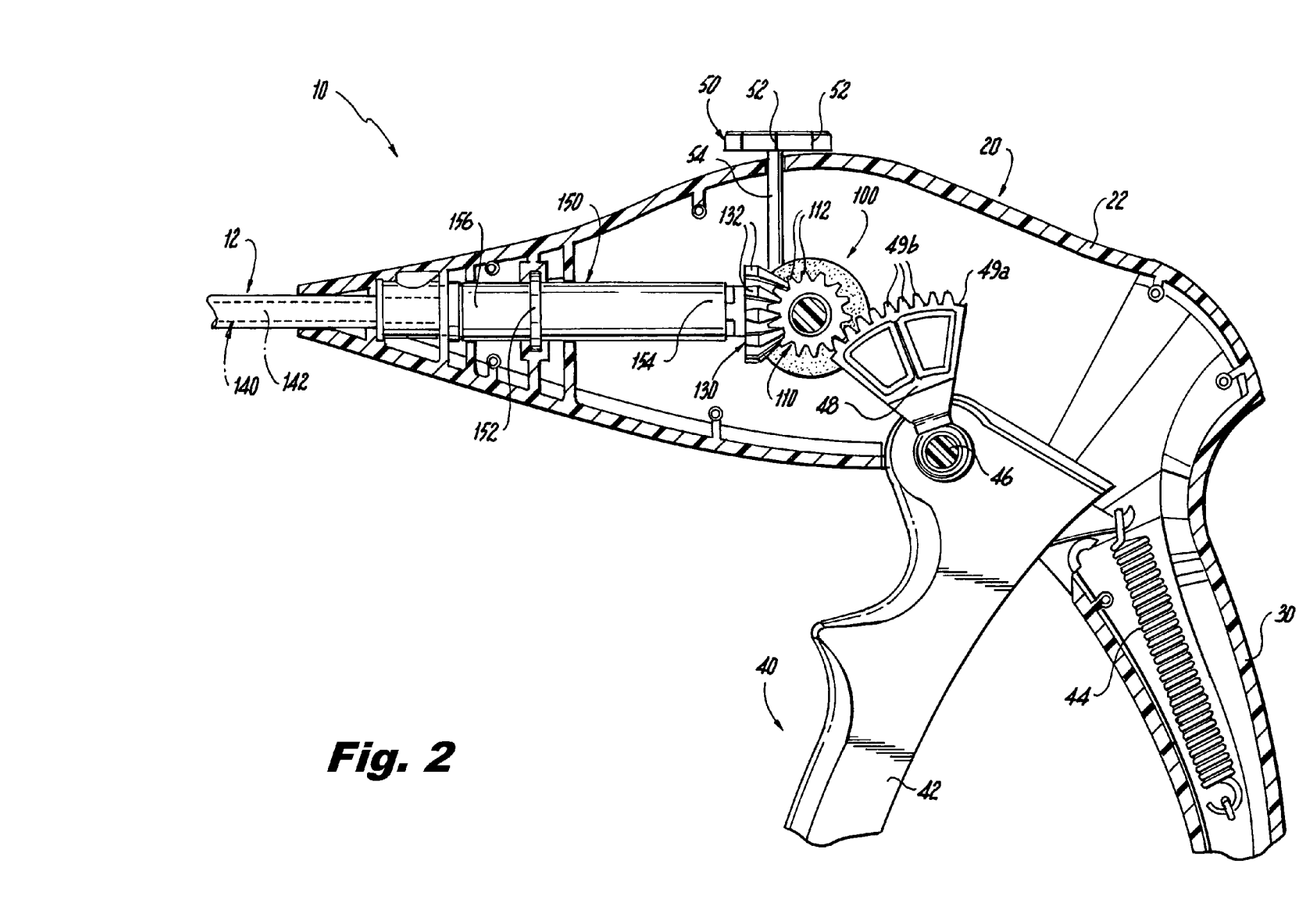
FIG. 2 is a side view of the proximal end of the surgical fastener applier of FIG. 1 with a portion of the housing removed to show the internal components thereof.

As best shown in FIG. 2, trigger 40 is pivotably couple to housing 20 via a pivot pin 46, thus permitting trigger 40 to pivot about pivot pin 46 and relative to housing 20 between the spaced-apart and compressed positions. Trigger 40 further includes a flange portion 48 extending in a generally opposite direction from pivot pin 46 relative to grasping portion 42 of trigger 40. Flange portion 48 defines an arced surface 49a including a plurality of spaced-apart gear teeth 49b. Gear teeth 49b are configured to mesh with complementary gear teeth 112 of input pinion 110 of drive assembly 100 such that pivoting of trigger 40 from the spaced-apart position to the compressed position effects rotation of input pinion 110. Drive assembly 100 further includes an output pinion 120 (FIGS. 5A-5C) coupled to input pinion 110 via a variable drive mechanism 300 of drive assembly 100. Output pinion 120 (FIGS. 5A-5C) includes a plurality of gear teeth 122 (FIGS. 5A-5C) configured to mesh with complementary gear teeth 132 of gear cap 130. Gear cap 130 is coupled to a proximal end 142 of drive shaft 140, which is rotatably disposed within elongated tubular member 12. Thus, pivoting of trigger 40 from the spaced-apart position to the compressed position effects rotation of drive shaft 140. Variable drive mechanism 300 (FIGS. 5A-5C), which couples input and output pinions 110, 120 (FIGS. 5A-5C) to one another, is selectively adjustable, e.g., via rotation of control knob 50 (FIG. 1), to set the input to output ratio of drive assembly 100. In other words, variable drive mechanism 300 (FIGS. 5A-5C) sets the amount of rotation of drive shaft 140 (i.e., the output) per full compression of trigger 40 (i.e., the input).

Figure 3A:
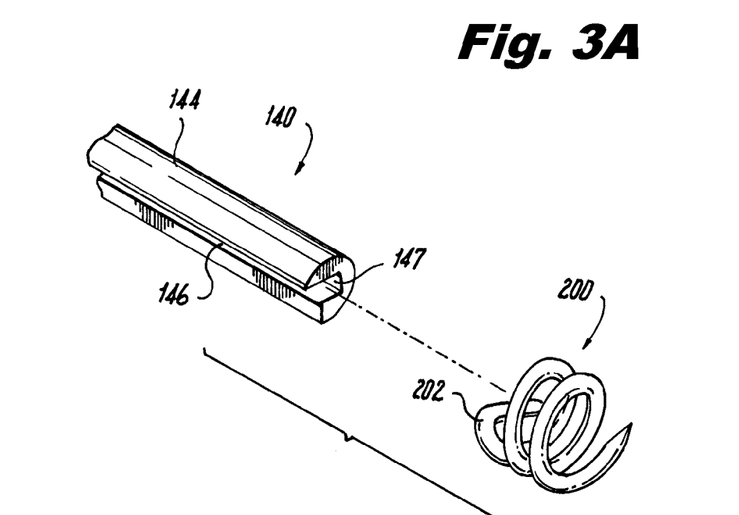
FIG. 3A is an exploded, front, perspective view of the distal end of the drive shaft including a surgical fastener configured for engagement at the distal end of the drive shaft.
Figure 3B:
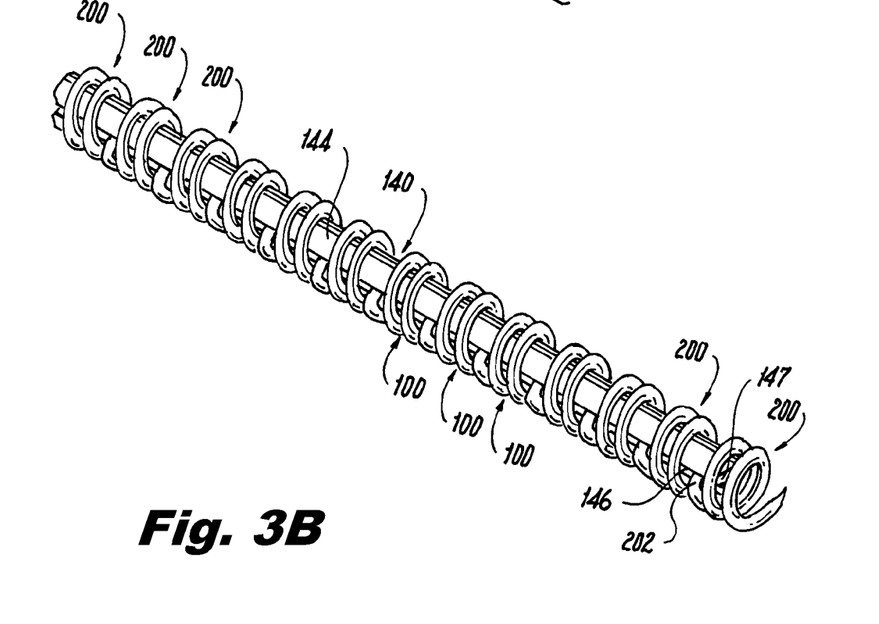
FIG. 3B is a front, perspective view of the distal end of the drive shaft of FIG. 3A including a plurality of surgical fasteners engaged on the drive shaft.

With additional reference to FIGS. 3A-3B, drive shaft 140 is configured to retain and drive one or more surgical fasteners 200. Drive shaft 140 includes a longitudinally-extending slot 146 extending along the length of a distal portion 144 of drive shaft 140. Slot 146 is configured to receive a tang 202 of each of the surgical fasteners 200 retained on drive shaft 140 such that rotation of drive shaft 140 effects similar rotation of surgical fasteners 200. Other suitable engagement mechanisms for rotatably engaging one or more surgical fasteners 200 on drive shaft 140 are also contemplated, depending on the configuration of the particular surgical fasteners 200 used. As mentioned above, gear cap 130 is coupled to proximal end 142 of drive shaft 140 to operably couple drive shaft 140 to drive assembly 100.

As shown in FIG. 3B, a plurality of surgical fasteners 200 are arranged longitudinally along the length of distal portion 144 of drive shaft 140 in end-to-end relation. Each surgical fastener 200 has its associated tang 202 positioned within slot 146 of drive shaft 140. In order to move successive surgical fasteners 200 in a distal direction upon rotation of drive shaft 140, a coiled spring may be fixedly disposed within drive shaft 140 and about surgical fasteners 200. Thus, upon rotation of drive shaft 140, surgical fasteners 200 are rotated and translated distally along drive shaft 140 and along the coil, and through elongated tubular member 12. Reference may be made to U.S. Pat. No. 5,830,221, entitled "Coil Fastener Applier" or U.S. Patent Publication No. 2011/0087240, filed on Oct. 20, 2010, entitled "Absorbable Fastener for Hernia Mesh Fixation," the entire contents of each of which being incorporated herein by reference, for an exemplary construction of elongated tubular member 12 or other components of surgical fastener applier 10.

Open distal end 147 of slot 146 of drive shaft 140 allows the distal-most surgical fastener 200 to be driven distally from drive shaft 140 and into tissue as the surgical fasteners 200 are rotated and translated distally along drive shaft 140. As can be appreciated, the size of the distal-most surgical fastener 200, e.g., the number of coil revolutions of the distal-most surgical fastener 200, determines the amount of rotation of drive shaft 140 required to fully drive the distal-most surgical fastener 200 from drive shaft 140 and into tissue.

Drive shaft 140 (or a portion thereof) may be formed integral with surgical fastener applier 10 or may be removably coupled thereto. In particular, drive shaft 140 may be fixedly coupled to gear cap 130 or may be releasably couplable to gear cap 130 via a coupling tube 150 that is rotatably mounted within housing 20 via a retaining ring 152.

With respect to embodiments where drive shaft 140 is releasably couplable, coupling tube 150 is coupled to gear cap 130 at a proximal end 154 of coupling tube 150 and is configured to releasably receive drive shaft 140 at its distal end 156. Drive shaft 140 may be configured to releasably engage distal end 156 of coupling tube 150 via a spring-biased latch engagement, friction-fitting, or other suitable releasable securement mechanism. Thus, prior to use, a replaceable cartridge, i.e., a drive shaft 140 retaining the desired size surgical fasteners 210, 220, 230 (FIGS. 4A-4C), may be inserted proximally through elongated tubular member 12 and into engagement with coupling tube 150.

Figure 4A:
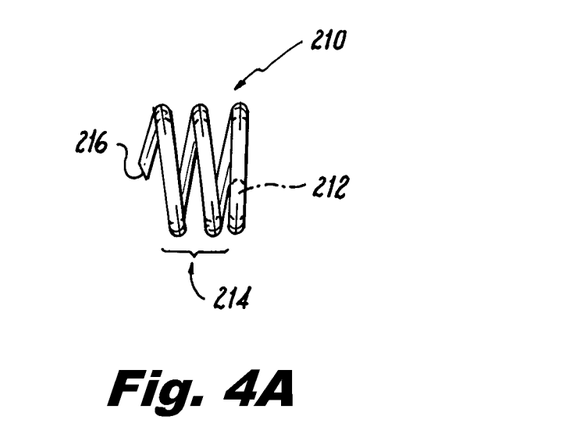
FIG. 4A is a side view of a first, relatively small-sized surgical fastener configured for use with the surgical fastener applier of FIG. 1.
Figure 4B:
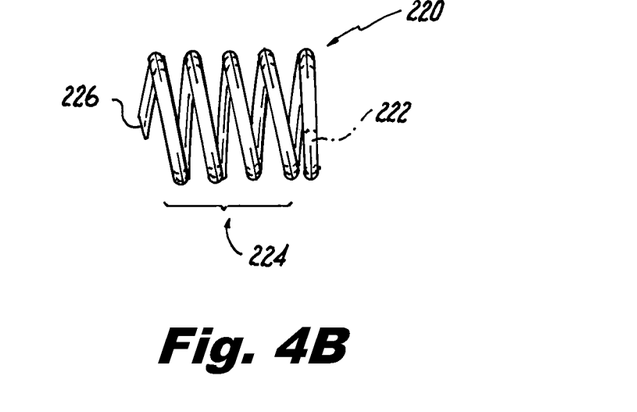
FIG. 4B is a side view of a second, medium-sized surgical fastener configured for use with the surgical fastener applier of FIG. 1.
Figure 4C:
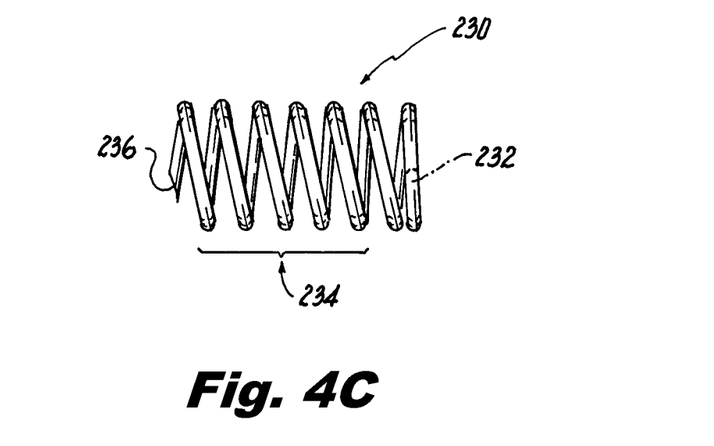
FIG. 4C is a side view of a third, relatively large-sized surgical fastener configured for use with the surgical fastener applier of FIG. 1.

It is envisioned that the various replaceable cartridges, e.g., drive shafts 140 retaining relatively small, medium, and relatively large surgical fasteners 210, 220, 230 (FIGS. 4A-4C), include different features and/or markings to allow a user to readily distinguish between the different size surgical fasteners 210, 220, 230 (FIGS. 4A-4C). For example, the drive shaft 140 of each replaceable cartridge may include indicia (not shown) disposed towards proximal end 142 thereof and configured to align with a transparent portion (or portions) of elongated tubular member 12 and/or housing 20 such that the user can visually confirm which replaceable cartridge is engaged within surgical fastener applier 10.

Alternatively or additionally, surgical fastener applier 10 may include a mechanical, electrical, or electromechanical sensor (not shown) configured to sense a particular feature of drive shaft 140 and/or the surgical fasteners 200 disposed about the drive shaft 140 to determine the size of surgical fasteners 200 loaded within surgical fastener applier 10.

In embodiments where drive shaft 140 is fixedly coupled to gear cap 130, surgical fasteners 200 may be loaded onto drive shaft 140 and into elongated tubular member 12 at the respective distal ends thereof, either individually or in a group(s), e.g., in a fastener-only replaceable cartridge.

Referring now to FIGS. 4A-4C, various differently-sized helical-shaped coil surgical fasteners 210, 220, 230, e.g., a relatively small-sized, medium-sized, and relatively large-sized surgical fastener 210, 220, 230, configured for use with surgical fastener applier 10 are shown. Surgical fasteners 210, 220, 230 are configured to be applied to tissue by being rotatably driven through tissue. Surgical fasteners 210, 220, 230 each include a coil body portion 214, 224, 234, a sharpened, tissue-penetrating distal tip 216, 226, 236, and a proximal tang 212, 222, 232 that extends generally inwardly for receipt within slot 146 of drive shaft 140 (FIGS. 3A-3B).

Coil body portions 214, 224, 234 of surgical fasteners 210, 220, 230 define approximately 2½, 4½, and 6½ coil revolutions, respectively, although other size surgical fasteners are also contemplated. As can be appreciated, a greater amount of rotation of drive shaft 140 (FIGS. 3A-3B) is required to apply surgical fastener 230 as compared to surgical fastener 210, while applying surgical fastener 220 requires a lesser amount of rotation of drive shaft 140 (FIGS. 3A-3B) as compared to surgical fastener 230 but a greater amount of rotation of drive shaft 140 (FIGS. 3A-3B) as compared to surgical fastener 210. Surgical fasteners 210, 220, 230 may be formed from any suitable biocompatible material, elastomeric or polymeric materials, metallic materials, and/or bioabsorbable or biodegradable materials.

Figure 5A:
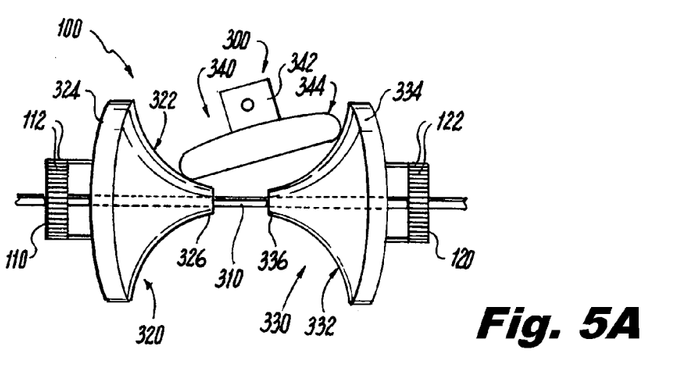
FIG. 5A is a top view of one embodiment of a drive assembly configured for use with the surgical fastener applier of FIG. 1 and shown in a first condition for applying relatively small-sized surgical fasteners.
Figure 5B:
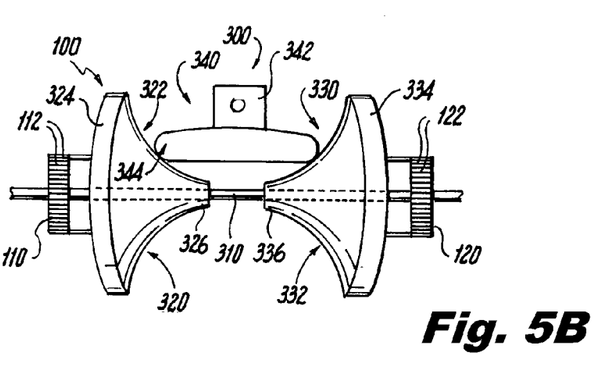
FIG. 5B is a top view of the drive assembly of FIG. 5A shown in a second condition for applying medium-sized surgical fasteners.
Figure 5C:
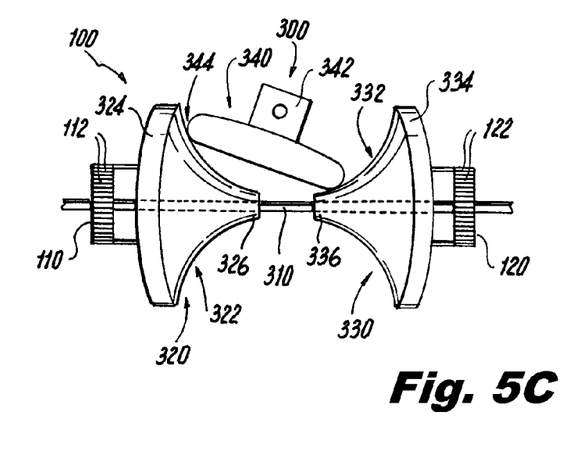
FIG. 5C is a top view of the drive assembly of FIG. 5A shown in a third condition for applying relatively large-sized surgical fasteners.

Turning now to FIGS. 5A-5C, one embodiment of a variable drive mechanism 300, provided in accordance with the present disclosure and configured for use with drive assembly 100, for selectively setting the input to output ratio of drive assembly 100, is shown. Variable drive mechanism 300 includes a transverse rod 310 having first and second rotating frusto-conical or cone members 320, 330, respectively, rotatably disposed about transverse rod 310, and a rotating disc member 340 coupled between first and second rotating cone members 320, 330. Transverse rod 310 may be fixed to housing 20 (FIGS. 1 and 2) or otherwise supported therein. First and second rotating cone members 320, 330 oppose one another and define planar or concave outer surfaces 322, 332 extending from the respective base portions 324, 334 to the respective apex portions 326, 336, thereof. Input pinion 110 of drive assembly 100 (FIG. 2) is engaged to first rotating cone member 320, while output pinion 120 of drive assembly 100 (FIG. 2) is engaged to second rotating cone member 330.

Disc member 340 is rotatably disposed on a support member 342. Disc member 340 defines a rounded outer surface 344 configured for frictional engagement with concave outer surfaces 322, 332 of first and second rotating cone members 320, 330 such that rotation of first rotating cone member 320 effects rotation of disc member 340 which, in turn, effects rotation of second rotating cone member 330 in an opposite direction as compared to first rotating cone member 320 and according to the set input to output ratio of variable drive mechanism 300. Disc member 340 is tiltable relative to first and second rotating cone members 320, 330 to vary the input to output ratio of variable drive mechanism 300, as will be described in greater detail below.

With particular reference to FIGS. 4A and 5A, in conjunction with FIGS. 1-3B, variable drive mechanism 300 is shown disposed in a first condition wherein the input to output ratio of variable drive mechanism 300 is greater than one. In this condition, disc member 340 is oriented such that rounded outer surface 344 of disc member 340 contacts concave outer surface 322 of first rotating cone member 320 towards apex portion 326 thereof (which defines a relatively small diameter) and such that rounded outer surface 344 of disc member 340 contacts concave outer surface 332 of second rotating cone member 330 towards base portion 334 thereof (which defines a relatively large diameter). As such, upon pivoting of trigger 40 from the spaced-apart position to the compressed position, input pinion 110 is rotated to thereby rotate first rotating cone member 320 about transverse rod 310. Rotation of first rotating cone member 320 effects rotation of disc member 340 which, in turn, effects rotation of second rotating cone member 330 in an opposite direction as compared to first rotating cone member 320. However, due to the tilted positioning of disc member 340 relative to first and second rotating cone members 320, 330, first rotating cone member 320 is rotated a relatively greater amount as compared to second rotating cone member 330. Thus, this first condition is suitable for applying relatively small-sized surgical fasteners 210 (FIG. 4A) without the need to shorten the stroke length of trigger 40, i.e., application of surgical fastener 210 (FIG. 4A) is effected via full compression of trigger 40.

With particular reference to FIGS. 4B and 5B, in conjunction with FIGS. 1-3B, variable drive mechanism 300 is shown disposed in a second condition wherein the input to output ratio of variable drive mechanism 300 is equal to one. In this condition, disc member 340 is oriented such that rounded outer surface 344 of disc member 340 contacts concave outer surfaces 322, 332 of first and second rotating cone members 320, 330 at similar intermediate positions (which define similar diameters). As such, upon pivoting of trigger 40 from the spaced-apart position to the compressed position, first and second rotating cone members 320, 330 are rotated a similar amount in opposite directions. Thus, this second condition is suitable for applying medium-sized surgical fasteners 220 (FIG. 4B) without the need to shorten or lengthen the stroke length of trigger 40, i.e., application of surgical fastener 210 (FIG. 4B) is effected via full compression of trigger 40.

With particular reference to FIGS. 4C and 5C, in conjunction with FIGS. 1-3B, variable drive mechanism 300 is shown disposed in a third condition wherein the input to output ratio of variable drive mechanism 300 is less than one. In this condition, disc member 340 is oriented such that rounded outer surface 344 of disc member 340 contacts concave outer surface 322 of first rotating cone member 320 towards base portion 324 thereof (which defines a relatively large diameter) and such that rounded outer surface 344 of disc member 340 contacts concave outer surface 332 of second rotating cone member 330 towards apex portion 336 thereof (which defines a relatively small diameter). As such, upon pivoting of trigger 40 from the spaced-apart position to the compressed position, input pinion 110 is rotated to rotate first and second rotating cone members 320, 330 in opposite directions. However, due to the positioning of disc member 340 relative to first and second rotating cone members 320, 330, second rotating cone member 330 is rotated a relatively greater amount as compared to first rotating cone member 320. Thus, this third condition is suitable for applying relatively large-sized surgical fasteners 230 (FIG. 4C) without the need to lengthen the stroke length of trigger 40, i.e., application of surgical fastener 230 (FIG. 4C) is effected via full compression of trigger 40.

Referring again to FIGS. 1 and 2, in conjunction with FIGS. 5A-5C, as mentioned above, control knob 50 is coupled to drive assembly 100 to permit a user to select a desired configuration of drive assembly 100, depending on the particular size surgical fastener 210, 220, 230 (FIGS. 4A-4C) to be applied. More specifically, control knob 50 includes a control shaft 54 that is operably coupled to support 342 of disc member 340 of variable drive mechanism 300 of drive assembly 100 such that rotation of control knob 50 tilts disc member 340 relative to first and second rotating cone members 320, 330, e.g., between the first, second, and third conditions.

Accordingly, in use, control knob 50 is rotated to a desired position corresponding to a desired tilt angle of disc member 340. Thus, upon compression of trigger 40 from the spaced-apart position to the compressed position, drive assembly 100 effects rotation of drive shaft 140 an appropriate amount for applying the particularly-sized surgical fastener 210, 220, 230 (FIGS. 4A-4C) from surgical fastener applier 10 into tissue.

In embodiments where a sensor (not shown) is provided, the sensor (not shown) may further be configured to sense a position of control knob 50 to indicate whether the position of control knob 50 corresponds to the size of surgical fasteners 210, 220, 230 (FIGS. 4A-4C) loaded within surgical fastener applier 10. Alternatively, the sensor (not shown) may be coupled to an automatic setting assembly (not shown) that performs the function of control knob 50 in accordance with the feedback received from the sensor (not shown).

Figure 6A:
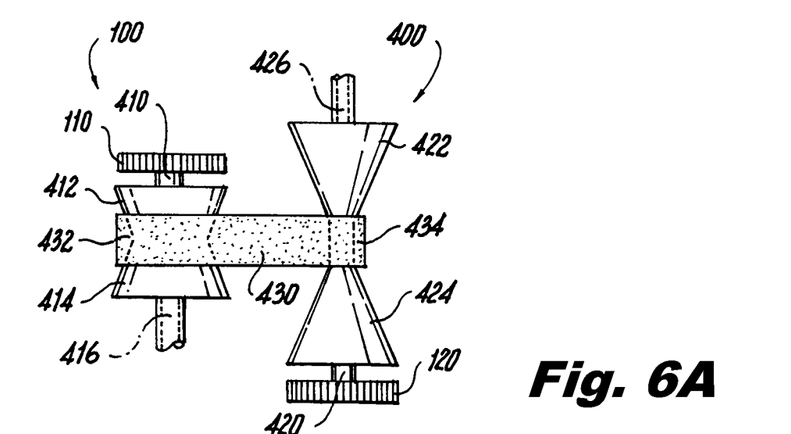
FIG. 6A is a top view of another embodiment of a drive assembly configured for use with the surgical fastener applier of FIG. 1 and shown in a first condition for applying relatively small-sized surgical fasteners.
Figure 6B:
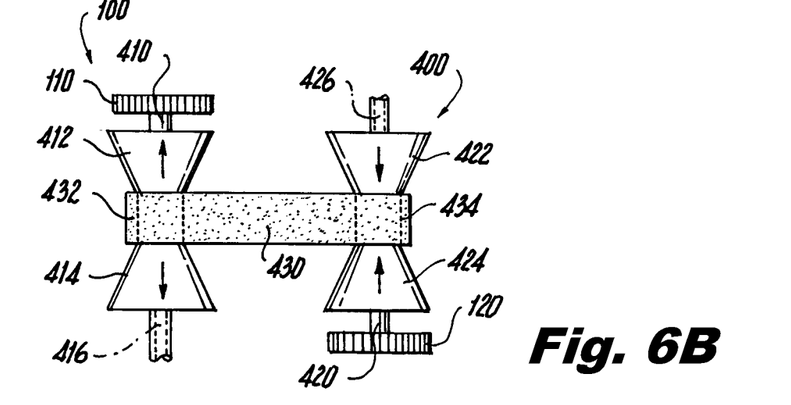
FIG. 6B is a top view of the drive assembly of FIG. 6A shown in a second condition for applying medium-sized surgical fasteners.
Figure 6C:
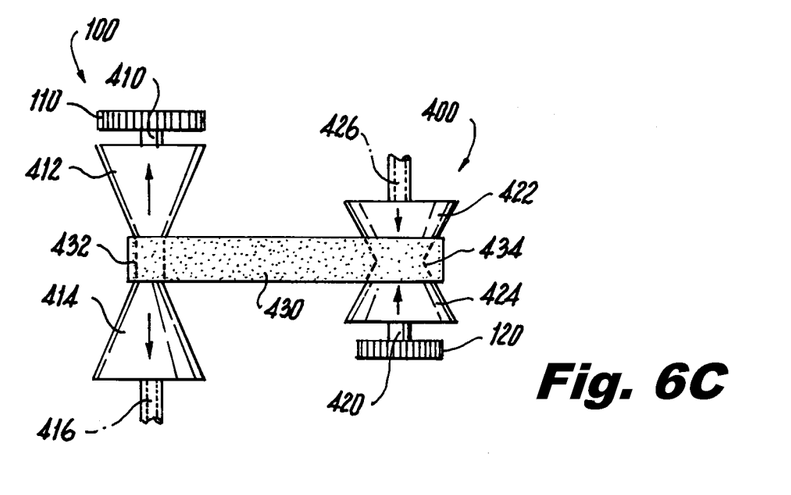
FIG. 6C is a top view of the drive assembly of FIG. 6A shown in a third condition for applying relatively large-sized surgical fasteners.

Turning now to FIGS. 6A-6C, another embodiment of a variable drive mechanism 400, provided in accordance with the present disclosure and configured for use with drive assembly 100, for selectively setting the input to output ratio of drive assembly 100, is shown. Variable drive mechanism 400 includes a proximal shaft 410 having first and second rotating cone members 412, 414, respectively, slidably disposed thereabout, and a distal shaft 420 having first and second rotating cone members 422, 424, respectively, slidably disposed thereabout. A belt 430, having a fixed length, disposed about both pairs of rotating cone members 412, 414 and 422, 424 interconnects proximal and distal shafts 410, 420, respectively. Proximal and distal shafts 410, 420 are rotatably disposed about proximal and distal transverse shafts 416, 426, respectively, which may be fixed to housing 20 (FIG. 1) or otherwise supported therein. Input pinion 110 of drive assembly 100 is engaged to proximal transverse shaft 416, while output pinion 120 of drive assembly 100 is engaged to distal transverse shaft 426.

As mentioned above, rotating cone members 412, 414, respectively, are slidably disposed about proximal shaft 410, while rotating cone members 422, 424, are slidably disposed about distal shaft 420. One or both of rotating cone members 412, 414 is movable relative to the other between a closer-together position and a further-spaced position. Likewise, one or both of rotating cone members 422, 424 is movable relative to the other between a closer-together position and a further-spaced position. Accordingly, with belt 430 disposed about rotating cone members 412, 414 and 422, 424, rotating cone members 412, 414 and 422, 424 of each pair may be moved relative to one another to vary the diameter about which belt 430 is rotated at the proximal and distal ends 432, 434, respectively, of belt 430. It is envisioned that the pairs of cone members 412, 414 and 422, 424 be moved in cooperation with one another to maintain a substantially constant tension on belt 430. By varying the relative diameter about which belt 430 is rotated at the proximal and distal ends 432, 434, respectively, thereof, the input to output ratio of variable drive mechanism 400 is varied. Control knob 50 (FIG. 1) may be operably coupled to variable drive mechanism 400 for moving rotating cone members 412, 414 and 422, 424, to thereby vary the input to output ratio of variable drive mechanism 400, similarly as described above with respect to variable drive mechanism 300 (FIGS. 5A-5C).

With particular reference to FIG. 6A, in conjunction with FIGS. 1-2, variable drive mechanism 400 is shown disposed in a first condition wherein the input to output ratio of variable drive mechanism 400 is greater than one. In this condition, first and second rotating cone members 412, 414 of proximal shaft 410 are disposed in the closer-together position such that the diameter about which belt 430 rotates at its proximal end 432 is relatively large. On the other hand, first and second rotating cone members 422, 424 of distal shaft 420 are disposed in the further-spaced position such that the diameter about which belt 430 rotates at its distal end 434 is relatively small. As such, upon pivoting of trigger 40 from the spaced-apart position to the compressed position, input pinion 110 is rotated to thereby rotate belt 430 which, in turn, effects rotation of output pinion 120 in the same direction as input pinion 110. However, due to the difference in diameters about which belt 430 rotates at its proximal and distal ends 432, 434, respectively, input pinion 110 is rotated a relatively greater amount as compared to output pinion 120. Thus, this first condition is suitable for applying relatively small-sized surgical fasteners 210 (FIG. 4A) without the need to shorten the stroke length of trigger 40, i.e., application of surgical fastener 210 (FIG. 4A) is effected via full compression of trigger 40.

With particular reference to FIG. 6B, in conjunction with FIGS. 1-2, variable drive mechanism 400 is shown disposed in a second condition wherein the input to output ratio of variable drive mechanism 400 is equal to one. In this condition, first and second rotating cone members 412, 414 and 422, 424 of proximal and distal shafts 41, 420 are similarly disposed in an intermediate positions such that the diameters about which belt 430 rotates at its proximal and distal ends 432, 434 are similar. As such, upon pivoting of trigger 40 from the spaced-apart position to the compressed position, input and output pinions 110, 120 are rotated similar amounts in a similar direction. Thus, this second condition is suitable for applying medium-sized surgical fasteners 220 (FIG. 4B) without the need to shorten or lengthen the stroke length of trigger 40, i.e., application of surgical fastener 220 (FIG. 4B) is effected via full compression of trigger 40.

With particular reference to FIG. 6C, variable drive mechanism 400 is shown disposed in a third condition wherein the input to output ratio of variable drive mechanism 400 is less than one. In this condition, first and second rotating cone members 412, 414 of proximal shaft 410 are disposed in the further-spaced position such that the diameter about which belt 430 rotates at its proximal end 432 is relatively small. On the other hand, first and second rotating cone members 422, 424 of distal shaft 420 are disposed in the closer-together position such that the diameter about which belt 430 rotates at its distal end 434 is relatively large. As such, upon pivoting of trigger 40 from the spaced-apart position to the compressed position, input pinion 110 is rotated to thereby rotate belt 430 which, in turn, effects rotation of output pinion 120 in the same direction as input pinion 110. However, due to the difference in diameters about which belt 430 rotates at its proximal and distal ends 432, 434, respectively, output pinion 120 is rotated a relatively greater amount as compared to input pinion 110. Thus, this third condition is suitable for applying relatively large-sized surgical fasteners 230 (FIG. 4C) without the need to lengthen the stroke length of trigger 40, i.e., application of surgical fastener 230 (FIG. 4C) is effected via full compression of trigger 40.

Although variable drive mechanisms 300, 400 are described above with respect to first, second, and third conditions, variable drive mechanisms 300, 400 may be continuously transitioned to define any suitable input to output ratio, as desired. Control knob 50 may also be configured to permit continuous transitioning of variable drive mechanisms 300, 400, as opposed to defining pre-determined intervals corresponding to one or more input to output ratios (as described above).

Referring again to FIGS. 1-4C, the use and operation of surgical fastener applier 10 is described. Initially, the user selects a desired size surgical fastener(s) 210, 220, 230 to be used, e.g., in accordance with anatomical considerations, the particular procedure to be performed, etc., and loads the selected surgical fasteners 210, 220, 230 into surgical fastener applier 10. In particular, a drive shaft 140 retaining the desired size surgical fasteners 210, 220, 230 is inserted proximally through elongated tubular member 12 and into engagement with coupling tube 150. The size of the surgical fasteners 210, 220, 230 may then be visually or otherwise confirmed, as mentioned above, such that control knob 50 may be set to the appropriate setting. That is, where relatively small-sized surgical fasteners 210 are loaded into surgical fastener applier 10, control knob 50 is rotated to the appropriate position to transition variable drive mechanisms 300, 400 (FIGS. 5A-5C and 6A-6C) to the first condition; where medium-sized surgical fasteners 220 are loaded into surgical fastener applier 10, control knob 50 is rotated to the appropriate position to transition variable drive mechanism (FIGS. 5A-5C and 6A-6C) to the second condition; and where relatively large-sized surgical fasteners 230 are loaded into surgical fastener applier 10, control knob 50 is rotated to the appropriate position to transition variable drive mechanism (FIGS. 5A-5C and 6A-6C) to the third condition. With surgical fasteners 210, 220, 230 loaded into surgical fastener applier 10 and variable drive mechanism (FIGS. 5A-5C and 6A-6C) disposed in the appropriate condition, surgical fastener applier 10 is ready for use.

Once ready for use as described above, elongated tubular member 12 of surgical fastener applier 10 is inserted through an access portal (not shown) and/or cannula structure (not shown) into an endoscopic surgical site, or, in an open surgical procedure, is simply positioned adjacent the surgical site. With surgical fastener applier 10 positioned as desired, trigger 40 is fully compressed from the spaced-apart position to the compressed position. As detailed above, depending on the setting of variable drive mechanism (FIGS. 5A-5C and 6A-6C), drive shaft 140 is rotated an appropriate and sufficient amount upon full compression of trigger 40 so as to rotatably drive the distal-most surgical fastener 210, 220, 230 from drive shaft 140 and elongated tubular member 12 into tissue. More specifically, with relatively small-sized surgical fasteners 210 loaded into surgical fastener applier 10 and with variable drive mechanism (FIGS. 5A-5C and 6A-6C) set in the first condition, full compression of trigger 40 rotates drive shaft 140 approximately 2½ revolutions to apply the relatively small-sized surgical fastener 210 (of about 2½ revolutions) to tissue; with medium-sized surgical fasteners 220 loaded into surgical fastener applier 10 and with variable drive mechanism (FIGS. 5A-5C and 6A-6C) set in the second condition, full compression of trigger 40 rotates drive shaft 140 approximately 4½ revolutions to apply the medium-sized surgical fastener 220 (of about 4½ revolutions) to tissue; and with relatively large-sized surgical fasteners 230 loaded into surgical fastener applier 10 and with variable drive mechanism (FIGS. 5A-5C and 6A-6C) set in the third condition, full compression of trigger 40 rotates drive shaft 140 approximately 6½ revolutions to apply the relatively large-sized surgical fastener 230 (of about 6½ revolutions) to tissue. The above-described process may subsequently be repeated for applying additional surgical fasteners 210, 220, 230 to tissue.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:
1. A surgical fastener applier, comprising:
 a housing having an elongated tubular member extending distally from the housing;
 a trigger coupled to an input member and extending from the housing, the trigger pivotable relative to the housing from a first position to a second position to rotate the input member a fixed amount;
 a drive shaft extending from the housing and rotatably disposed within the elongated tubular member, the drive shaft retaining at least one surgical fastener thereon, the drive shaft coupled to an output member at a proximal end of the drive shaft such that rotation of the output member effects corresponding rotation of the drive shaft to apply a distal-most surgical fastener to tissue; and a variable drive mechanism disposed within the housing and operably coupled between the input member and the output member, the variable drive mechanism transitionable between at least a first condition, wherein rotation of the input member by the fixed amount effects rotation of the output member a first amount, and a second condition, wherein rotation of the input member by the fixed amount effects rotation of the output member a second amount different from the first amount.

2. The surgical fastener applier according to claim 1, wherein the trigger includes a flange portion defining a plurality of gear teeth and wherein the input member defines a plurality of complementary gear teeth disposed in meshed engagement with the gear teeth of the flange portion of the trigger such that pivoting of the trigger from the first position to the second position rotates the input member the fixed amount.

3. The surgical fastener applier according to claim 1, wherein the drive shaft includes a gear cap disposed at the proximal end of the shaft, the gear cap defining a plurality of gear teeth, and wherein the output member defines a plurality of complementary gear teeth disposed in meshed engagement with the gear teeth of the gear cap such that rotation of output member corresponding rotation of the drive shaft to apply the distal-most surgical fastener to tissue.

4. The surgical fastener applier according to claim 1, further comprising a control knob coupled to the variable drive mechanism and extending from the housing, the control knob selectively manipulatable to transition the variable drive mechanism between the first and second conditions.

5. The surgical fastener applier according to claim 4, wherein at least one of the control knob and the housing includes indicia configured to indicate the condition of the variable drive mechanism.

6. The surgical fastener applier according to claim 1, wherein rotation of the output member by the first amount effects rotation of the drive shaft sufficiently for applying a first surgical fastener, and wherein rotation of the output member by the second amount effects rotation of the drive shaft sufficiently for applying a second surgical fastener larger than the first surgical fastener.

7. The surgical fastener applier according to claim 6, wherein the variable drive mechanism is transitionable to a third condition, wherein rotation of the input member by the fixed amount effects rotation of the output member a third amount different from the first and second amounts, and wherein rotation of the output member by the third amount effects rotation of the drive shaft sufficiently for applying a third surgical fastener larger than the first surgical fastener and smaller than the second surgical fastener.

8. The surgical fastener applier according to claim 1, wherein the drive shaft and the at least one surgical fastener comprise a replaceable cartridge, the replaceable cartridge releasably engagable with the surgical fastener applier, wherein the replaceable cartridge includes one of: a first drive shaft retaining a plurality of first surgical fasteners thereon, and a second drive shaft retaining a plurality of second larger surgical fasteners thereon.

9. The surgical fastener applier according to claim 1, wherein the variable drive mechanism includes first and second cone members and a disc member, each cone member defining an apex portion and a base portion having a diameter greater than that of the apex portion, the disc member interdisposed between the cone members and contacting each of the cone members such that the disc member imparts rotation of the first cone member to the second cone member, the disc member tiltable relative to the cone members to vary relative contact points between the disc member and the first and second cone members to thereby vary a ratio of rotation of the first cone member as compared to rotation of the second cone member.

10. The surgical fastener applier according to claim 9, wherein the input member is engaged to the first cone member and wherein the output member is engaged to the second cone member such that tilting the disc member varies a ratio of rotation of the input member as compared to rotation of the output member.

11. The surgical fastener applier according to claim 1, wherein the variable drive mechanism is continuously transitionable between at least the first and second conditions.

12. The surgical fastener applier according to claim 1, wherein the variable drive mechanism includes first and second pairs of cone members and a belt member disposed about the first and second pairs of cone members, the cone members of the first pair disposed about a first shaft and movable relative to one another along the first shaft to vary a first diameter about which the belt is disposed at a first end of the belt, the cone members of the second pair disposed about a second shaft and movable relative to one another along the second shaft to vary a second diameter about which the belt is disposed at a second end of the belt, wherein varying the first and second diameters relative to one another varies a ratio of rotation of the first pair of cone member as compared to rotation of the second pair of cone members.

13. The surgical fastener applier according to claim 12, wherein the input member is engaged to the first shaft and wherein the output member is engaged to the second shaft such that varying the first and second diameters relative to one another varies a ratio of rotation of the input member as compared to rotation of the output member.

14. A surgical kit, comprising:

first, second, and third cartridges, each cartridge including a drive member having a plurality of surgical fasteners disposed thereon, the first cartridge including surgical fasteners of a first size requiring a first amount of rotation for applying the first-sized surgical fasteners, the second cartridge including surgical fasteners of a second size requiring a second amount of rotation for applying the second-sized surgical fasteners, and the third cartridge including surgical fasteners of a third size requiring a third amount of rotation for applying the third-sized surgical fasteners; and a surgical fastener applier, including:

a housing having an elongated tubular member extending distally from the housing;

a trigger coupled to an input member and extending from the housing, the trigger pivotable relative to the housing from a first position to a second position to rotate the input member a fixed amount;

an output member configured to relesably engage each of the first, second, and third cartridges; and a variable drive mechanism disposed within the housing and operably coupled between the input member and the output member, the variable drive mechanism transitionable between a first condition, wherein rotation of the input member by the fixed amount effects rotation of the output member the first amount for applying the surgical fasteners of the first size when the first cartridge is engaged to the output member; a second condition, wherein rotation of the input member by the fixed amount effects rotation of the output member the second amount for applying the surgical fasteners of the second size when the second cartridge is engaged to the output member; and a third condition, wherein rotation of the input member by the fixed amount effects rotation of the output member the third amount for applying the surgical fasteners of the third size when the third cartridge is engaged to the output member.

* * * * *